(12) United States Patent
Murphy

(10) Patent No.: US 6,394,967 B1
(45) Date of Patent: *May 28, 2002

(54) METHOD AND APPARATUS FOR DISPLAYING LUNG SOUNDS AND PERFORMING DIAGNOSIS BASED ON LUNG SOUND ANALYSIS

(76) Inventor: Raymond L. H. Murphy, 38 Cypress Rd., Wellesley, MA (US) 02181

( * ) Notice: Subject to any disclaimer, the term of this patent is extended or adjusted under 35 U.S.C. 154(b) by 0 days.

This patent is subject to a terminal disclaimer.

(21) Appl. No.: 09/699,546

(22) Filed: Oct. 30, 2000

Related U.S. Application Data

(63) Continuation of application No. 09/172,343, filed on Oct. 14, 1998, now Pat. No. 6,139,505.

(51) Int. Cl.[7] .................................................. A61B 5/00
(52) U.S. Cl. ...................................... 600/586; 600/529
(58) Field of Search ................................. 600/508–509, 600/513, 528–529, 531–538; 381/67, 92

(56) References Cited

U.S. PATENT DOCUMENTS

| | | |
|---|---|---|
| 3,990,435 A | 11/1976 | Murphy |
| 4,063,550 A | 12/1977 | Tiep |
| 4,267,845 A | 5/1981 | Robertson, Jr. et al. |
| 4,672,977 A | 6/1987 | Kroll |
| 4,928,705 A | 5/1990 | Sekhar et al. |
| 4,951,678 A | 8/1990 | Joseph et al. |
| 4,991,581 A | 2/1991 | Andries |
| 5,010,889 A | 4/1991 | Bredesen et al. |
| 5,035,247 A | 7/1991 | Heimann |
| 5,165,417 A | 11/1992 | Murpphy, Jr. |
| 5,213,108 A | 5/1993 | Bredesen et al. |
| 5,218,969 A | 6/1993 | Bredesen et al. |
| 5,301,679 A | 4/1994 | Taylor |
| 5,329,932 A | 7/1994 | Yount |
| 5,825,895 A | 10/1998 | Grasfield et al. |
| 5,844,997 A | 12/1998 | Murphy, Jr. |
| 6,005,951 A | 12/1999 | Grasfield et al. |
| 6,116,241 A | 9/2000 | Huygen et al. |
| 6,139,505 A * | 10/2000 | Murphy ...................... 600/532 |
| 6,168,568 B1 * | 1/2001 | Gavriely ..................... 600/529 |

* cited by examiner

*Primary Examiner*—Robert L. Nasser
(74) *Attorney, Agent, or Firm*—Cesari and McKenna, LLP

(57) ABSTRACT

A lung sound diagnostic system for use in collecting, organizing and analyzing lung sounds associated with the inspiration(s) and expiration(s) of a patient. The system includes a plurality of transducers that may be placed at various sites around the patient's chest. The microphones are coupled to signal processing circuitry and A/D converters which digitize the data and preferably provides the digital data to a computer station. A data collection and organization program, executing on the computer station, organizes and formats the data into a combination display for display or printing. The combinational display includes at least two display elements. In a first display element, the data is shown for both inspiration and expiration combined in a first time scale. In a second display element, the data for inspiration and expiration are shown individually in a second time scale that is time-expanded relative to the first time scale. The system may also include application programs for detecting and classifying abnormal sounds. The resulting information may be displayed in a variety of formats to facilitate diagnosis. Additionally, the system may include an analysis program for comparing selected criteria corresponding to the detected abnormal sounds with predefined thresholds in order to provide a likely diagnosis.

19 Claims, 12 Drawing Sheets

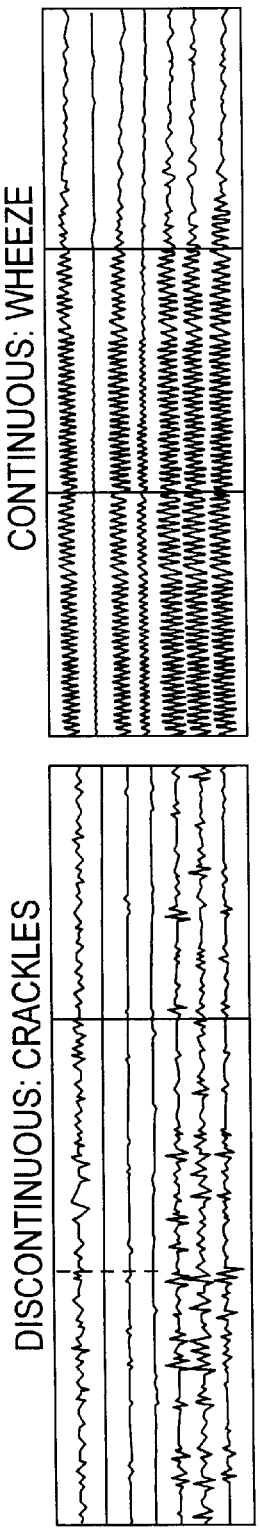
FIG. 6A  
FIG. 6B
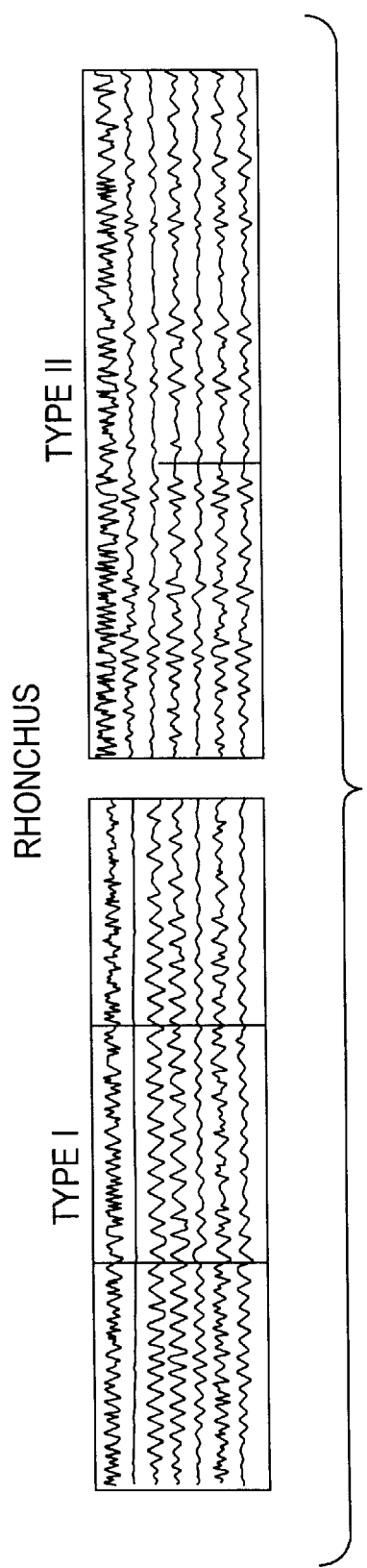
FIG. 6C

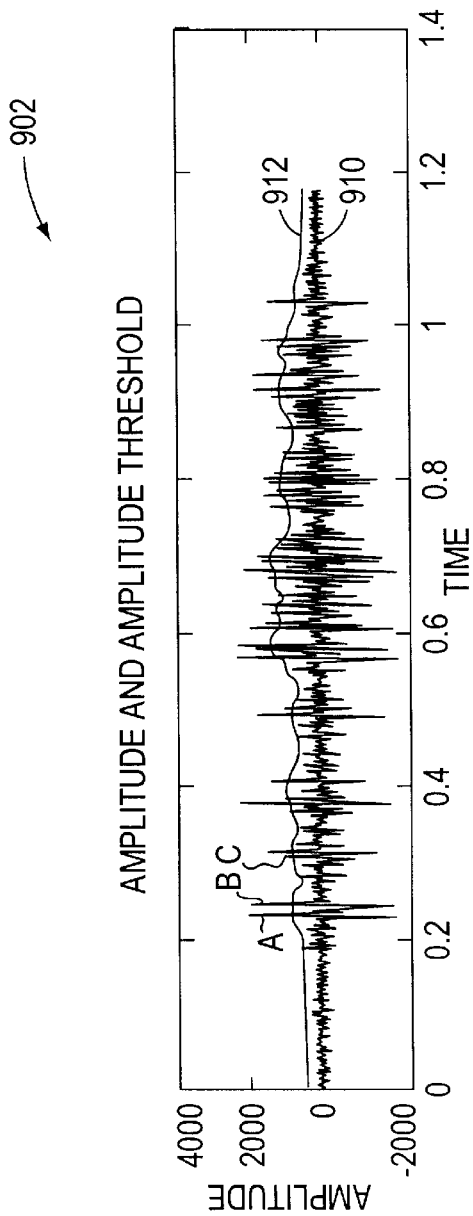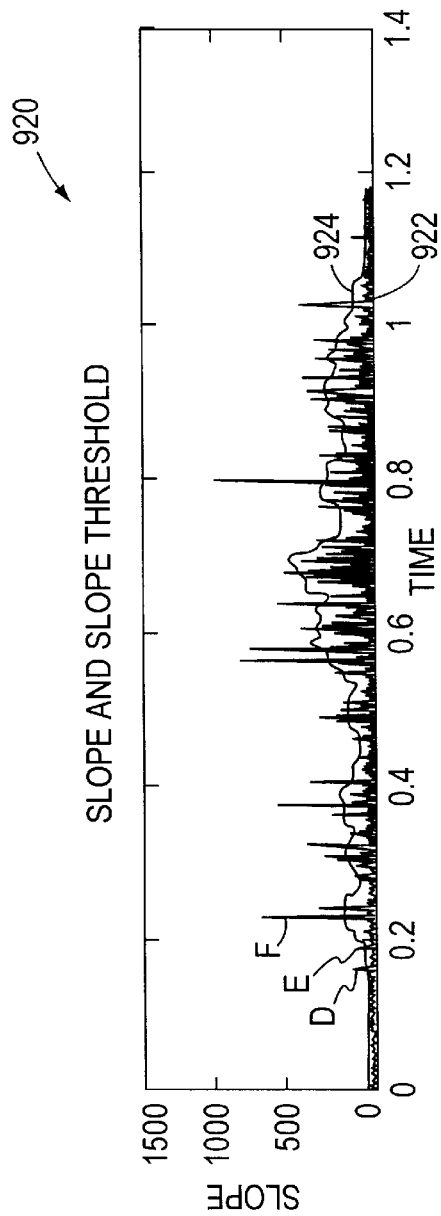

METHOD AND APPARATUS FOR DISPLAYING LUNG SOUNDS AND PERFORMING DIAGNOSIS BASED ON LUNG SOUND ANALYSIS

This application is a continuation of application Ser. No. 09/172,343 for Method and Apparatus for Displaying Lung Sounds and Performing Diagnosis Based on Lung Sound Analysis, filed on Oct. 14, 1998, now U.S. Pat. No. 6,139,505.

FIELD OF THE INVENTION

The present invention relates generally to non-invasive diagnostic systems and techniques, and more specifically, to a method and apparatus for diagnosis, based upon the review and analysis of lung sounds.

BACKGROUND OF THE INVENTION

Since the time of its invention in the early 1800's, the stethoscope has been used routinely by physicians to amplify sounds in the human body. The physician typically places the chest piece of the stethoscope against the patient's skin and listens through the stethoscope's earpieces. By monitoring a patient's breathing, a physician may detect the existence of adventitious (i.e., abnormal and/or unexpected) lung sounds. The identification and classification of adventitious lung sounds, moreover, often provides substantial information about pulmonary and associated abnormalities.

Adventitious lung sounds may be classified into two major types: pulmonary and pleural. Pulmonary lung sounds, moreover, may be categorized as crackles (or rales), which are discontinuous (i.e., interrupted) sounds, and wheezes and rhonchi, which are continuous. Crackles may be further classified as coarse, medium or fine, depending on their frequency, characteristics and amplitude. Wheezes may be similarly classified as sibilant or sonorous. An experienced and knowledgeable physician, moreover, may be able to diagnose certain pulmonary diseases, such as pneumonia, asthma, etc., simply by detecting, identifying and noting the location of particular adventitious sounds.

Lung sounds may also be recorded and displayed to assist in the detection and identification of adventitious sounds. For example, U.S. Pat. No. 3,990,435, entitled BREATH SOUND DIAGNOSTIC APPARATUS to Raymond L. H. Murphy, Jr., the inventor herein, discloses a system for providing a time-expanded visual display of lung sounds. That is, the time scale of the tracing or waveform detected by a microphone, normally plotted at approximately 25–50 mm/sec. by standard medical strip charts, is expanded to approximately 800 mm/sec. Expanding the time scale of the waveform significantly improves the physician's ability to detect and identify adventitious sounds.

Devices to analyze recorded lung sounds are also known. For example, U.S. Pat. No. 5,010,889, entitled INTELLIGENT STETHOSCOPE to Bredesen et al., discloses a stethoscope capable of digitizing and storing body sounds, including heart and lung sounds, in a memory structure configured to store up to six different sounds. The stethoscope includes a single chest piece with a microphone which may be moved to one of six locations around the patient's chest. The stethoscope further includes an LCD panel for displaying the waveform of a recorded sound.

Using waveform signature analysis, each of the six recorded waveforms is examined to determine the presence of high-pitch sounds which may correspond to fine crackles or low-pitch sounds which may correspond to coarse crackles. The presence or absence of these sounds is then formed into an array that may be compared with pre-recorded arrays corresponding to known conditions, e.g., normal lung sounds, pneumonia, etc. If a match is found between the recorded waveforms and one of the pre-recorded arrays, a diagnosis may be displayed on the LCD panel of the stethoscope.

Although Bredesen's intelligent stethoscope represents an improvement in diagnostic tools, especially for physicians lacking extensive experience in detecting and identifying adventitious lung sounds, it nonetheless has several disadvantages. First, the intelligent stethoscope has only a single microphone, so that obtaining recordings at multiple locations is time consuming. A single microphone also makes it impossible to record a given sound (e.g., a particular inspiration or expiration) from more than one point on the chest. Second, the small LCD panel is capable of displaying only a single waveform in one predefined format and is provided simply to determine whether valid data has been obtained. Due to these limitations, the intelligent stethoscope is not that likely to provide accurate diagnoses.

SUMMARY OF THE INVENTION

It is an object of the present invention to provide an improved method and apparatus for facilitating the diagnosis of certain diseases based upon recording, review and analysis of lung sounds.

In is a further object of the present invention to provide an improved method and apparatus that provides the diagnostician with a richer, more fully coordinated set of data for rapidly and accurately detecting lung sound abnormalities.

Another object of the present invention is to provide a system configured to generate graphical displays of detected abnormal lung sounds to facilitate diagnosis.

A still further object of the present invention is to provide a system for automatically providing an accurate diagnosis based upon an analysis of recorded lung sounds.

Briefly, the invention relates to a system for recording, displaying and analyzing lung sounds to facilitate the diagnosis of various pulmonary diseases. The system includes a plurality of transducers, such as microphones, that may be placed at preselected sites around a patient's chest. The transducers detect the sound or vibration of the body at these sites. The system also includes signal processing circuitry for conditioning and converting analog signals generated by the transducers into digital data. Additionally, the system includes a computer station coupled to the signal processing and digitizing circuitry. The computer station includes a processor, input/output circuitry, a data storage device, at least one input device, such as a keyboard or a mouse, and a graphical user interface. The system may further include a printer. Executing on the computer station is a first application program that collects and organizes the digital data for display on the graphical user interface and/or for printing preferably in a vertically arranged, combinational format that facilitates accurate diagnosis of various diseases.

More specifically, eight or more transducers are preferably applied simultaneously to obtain lung sound information, although a lesser number may be used sequentially to obtain at least eight different lung sound recordings. In response to the patient's inspiration and expiration, each transducer generates analog signals that are conditioned and digitized by the signal processing circuitry and stored by the computer station at the data storage device. In a preferred embodiment, sixteen transducers are used simultaneously with fifteen arranged around the patient's chest and one situated at the patient's trachea. The first application program organizes the received data from all sites for simultaneous display on the graphical user interface and/or printing in multiple time scales preferably in a vertical stack arrangement, such that all of the information may be reviewed concurrently by an attending physician. That is, the data or traces from the various transducers are plotted on the same graph, but vertically offset from each other, thereby allowing a comparison of sounds occurring simultaneously at different sites on the patient's chest. In particular, for each site, the data from the several transducers is preferably displayed or printed as a function of time in the following formats: (1) several repetitions of inspiration and expiration combined and unexpanded in time (e.g., in a time scale on the order 20–50 mm/sec.); and (2) inspiration and expiration separately and each slightly time-expanded (e.g., on the order of 200–400 mm/sec.). In a further embodiment, a third format in which inspiration and expiration are displayed separately with each fully time-expanded (e.g., on the order of 800 mm/sec.) is also included. By displaying or printing the data in this manner, the occurrence and identity of any abnormal sounds recorded at the various sites may be quickly and easily determined.

In addition, by comparing the displayed or printed combinational data with predefined criteria or guidelines, an accurate diagnosis may be reached. For example, if the review of the data reveals that the patient's expiration is on the order of 60% longer than the period of inspiration and crackles are found early during inspiration, then the data is determined to be characteristic of a patient with chronic obstructive pulmonary disease (COPD). Similarly, if expiration is only slightly longer than inspiration (e.g., 20% longer), inspiration sounds are distributed relatively uniformly over the chest, and there are few, if any, abnormal sounds, then the data is determined to be characteristic of a normal, healthy person. Similar criteria or guidelines have been developed for use in diagnosing asthma and interstitial pulmonary fibrosis (IPF). A display of the data in the above-described format lends itself to determining whether the predefined criteria have been met. The present invention thus facilitates the diagnosis of disease, often with better accuracy than other non-invasive techniques, as x-rays.

In a further embodiment of the present invention, a second application program, also executing on the computer station, analyzes the data recorded by the transducers. In particular, the second application program preferably includes means for identifying and counting the number and time of occurrence of adventitious sounds, such as wheezes, rhonchi and crackles, and categorizing the identified crackles as fine, medium or coarse. The second application program may also include means for performing other quantitative analysis, such as the ratio of duration of inspiration to expiration and statistical analysis of the intensity of the recorded sounds. This information may then be provided to the attending physician in a variety of ways. For example, it may be displayed in tabular format or graphically in relation to the point on the patient's chest at which the abnormal sound occurred.

A third application for generating a possible diagnosis may also be included. The third application may be a data analysis program, such as a neural network module or a statistical analysis module using multiple logistic regression models, that interoperates with a database of pre-classified lung sounds. Specifically, the database preferably includes multiple data sets for normal lungs sounds and lung sounds associated with specific diseases, such as COPD, asthma, and IPF. The database may be used to train a neural network classifier or to perform a statistical classification. The neural network module analyzes various quantities computed from the patient's lung sounds in view of the training database and, if a match of sufficient reliability is found, presents a preliminary diagnosis and corresponding probability.

BRIEF DESCRIPTION OF THE DRAWINGS

The above and further advantages of the invention may be better understood by referring to the following description in conjunction with the accompanying drawings, in which:

FIGS. 6A–C are exemplary plots of lung sound data versus time illustrating the appearance of several adventitious sounds;

FIGS. 9A and 9B and are data plots that may be generated by the adventitious sound detection application program;

DETAILED DESCRIPTION OF THE PREFERRED EMBODIMENT

Figure 1:
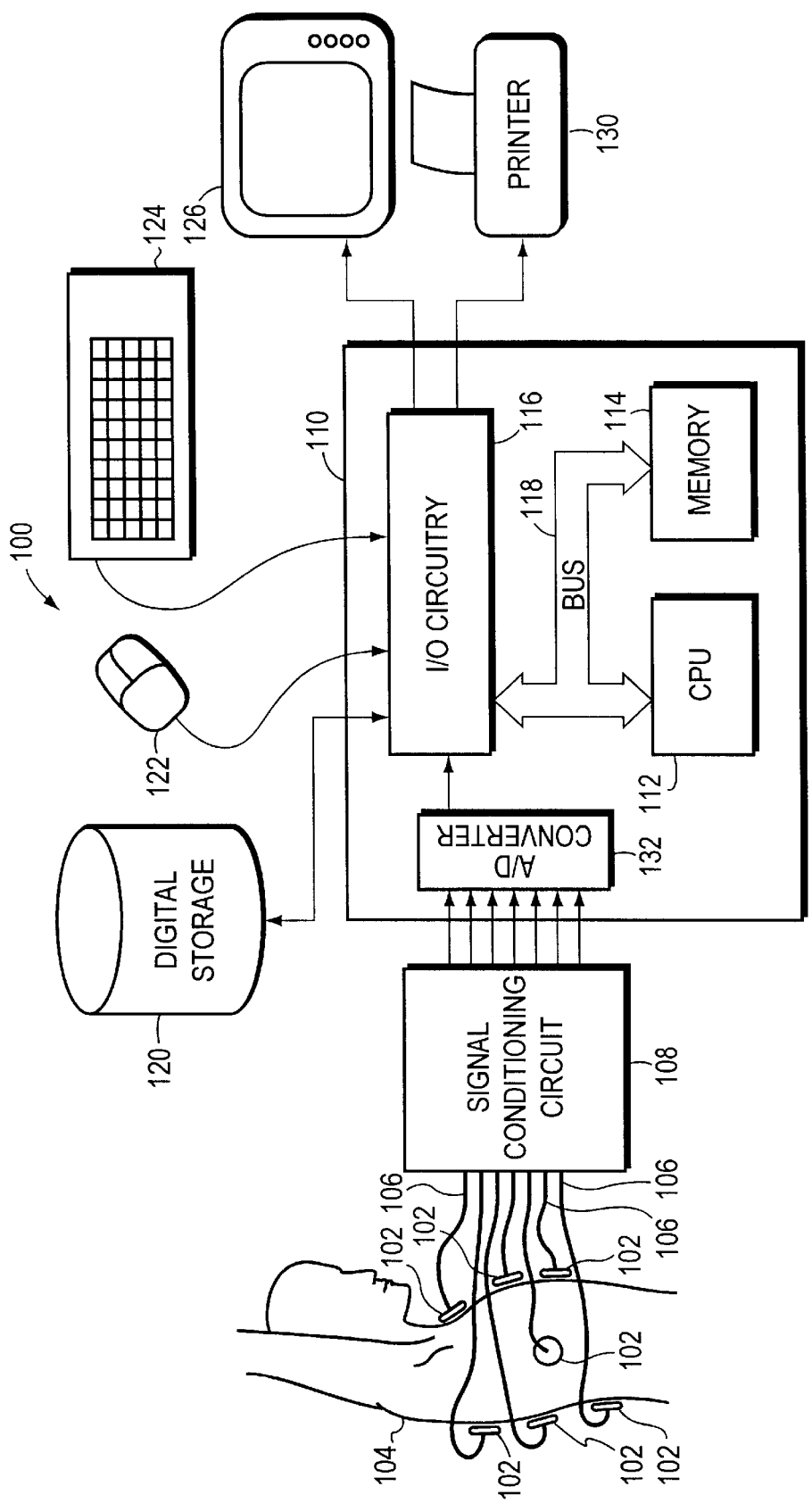
FIG. 1 is a block diagram of a system for implementing a preferred embodiment of the present invention.

FIG. 1 is a block diagram of the lung sound recording and analysis system 100 of the present invention. The system 100 includes a plurality of transducers, such as analog microphones 102, that may be placed at various sites around the chest of a patient 104. In the preferred embodiment of the invention, the system 100 uses sixteen different sites, of which, fifteen are located around the chest and one is located at the patient's trachea. More specifically, there is one site on the left side, one site on the right side, two sites on the upper front chest separated by the spinal column (proximate to the top portion of the lungs), one site on the lower right front chest, two sites on the upper back (proximate to the top portion of the lungs), four sites in the middle back (proximate to the mid portion of the lungs), four sites at the lower back (proximate to the bottom of the lungs) and one site at the trachea. It should be understood that other chest sites may be utilized by the system 100. Furthermore, a simpler system may use nine sites, eight around the chest and one at the trachea. The eight chest sites may include two on the upper front chest (separated by the spinal column), one on each side and four on the back (two upper and two lower) each pair separated by the spinal column.

Additionally, sixteen microphones 102, one located at each of the sites, are preferably utilized concurrently by the system 100 during the data collection process, although fewer are shown in FIG. 1 for clarity. This allows the data from all sites to be collected currently. Nonetheless, a simpler system may utilize one microphone 102 positioned sequentially at the nine or more sites for data collection and the data collection process repeated at each site. To isolate the microphones 102 from external sounds, they may be embedded in the chest pieces of conventional stethoscopes (not shown). The microphones 102 may also be taped or applied with suitable strapping to the patient 104 to prevent dislocation or movement during the data acquisition process.

Leads 106 extending from each microphone 102 are used to connect the microphones 102 to a signal conditioning circuit 108. In general, the signal conditioning circuit 108 modifies the analog audio signals generated by the microphones 102 in order to remove unwanted noise and boost the signal strength for subsequent digitizing. A suitable signal conditioning circuit for use in the present invention is disclosed in U.S. Pat. App. Ser. No. 08/729,272 filed Oct. 10, 1996, the specification of which is hereby incorporated by reference in its entirety.

The outputs from the signal conditioner 108 (i.e., processed audio signals from each microphone 102) are provided to a computer station 110. The computer station 110, which may be implemented, at least in part, using a personal computer or workstation, includes a central processing unit (CPU) 112 coupled to a memory 114 and input/output circuitry 116 by a bi-directional bus 118. The memory 114 typically comprises random access memory (RAM) for the temporary storage of information, including application programs and an operating system, and read only memory (ROM) for permanent storage of the computer's configuration and basic operating commands. The operating system controls the operations of the CPU 112.

The I/O circuitry 116 preferably connects the computer station 110 to a digital storage device 120, such as a disk drive or removable digital storage media, for storage of data as described below. The I/O circuitry 116 also connects the computer station 110 to cursor/pointer control and input devices, such as a mouse 122 and a keyboard 124. A window-based graphical user interface 126 and a printer 130 are also preferably connected to the I/O circuitry 116 of the computer station 110. The input/output circuitry 116 preferably contains the necessary hardware, e.g., buffers and adapters, needed to interface with the control devices 122, 124, the graphical user interface 126, printer 130, memory 114 and digital storage device 120.

The computer station 110 may be a personal computer of the IBM® series of computers sold by International Business Machines® or the Macintosh® series of computers sold by Apple Computer Inc. These computers have resident thereon, and are controlled and coordinated by, operating system software, such as IBM OS2®, Microsoft Windows 95® or Apple System 7® operating systems. It should be understood that the system 100 may also be implemented on other computer platforms, such as UNIX-based workstations manufactured and sold by Hewlett Packard.

As mentioned above, the signal conditioning circuit 108 is preferably connected to the computer station 110 such that the processed audio signals from each microphone 102 are received by computer station 110. Specifically, each output of signal conditioning circuit 108 (which preferably corresponds to a particular microphone 102) is connected to an analog-to-digital ("A/D") converter 132 that may be part of the computer station 110. The A/D converter 132 converts the processed analog audio information into a digital data stream. The sampling rate of the A/D converter 132 is preferably greater than 8000 samples per second and the bit rate is preferably greater than eight bits per sample.

Additionally, the A/D converter 132 synchronously pairs a master time signal from a system clock (not shown) with the digital audio information corresponding to each microphone 102. The master time signal provides a uniform time index to the signals received from the microphones 102. The paired digital-audio/time information associated with each microphone 102 is then forwarded to the digital storage device 120. The A/D converter 132 is preferably a multi-channel, high bandwidth data acquisition printed circuit board, such as those manufactured and sold by Keithley Metrabyte, Inc. It should be understood that the CPU 112, rather than the A/D converter 132, may pair the master clock signal to the digital audio information. It should be further understood that digital transducers, rather than analog microphones, may be utilized. The use of digital transducers would obviate the need for an A/D converter.

Figure 2:
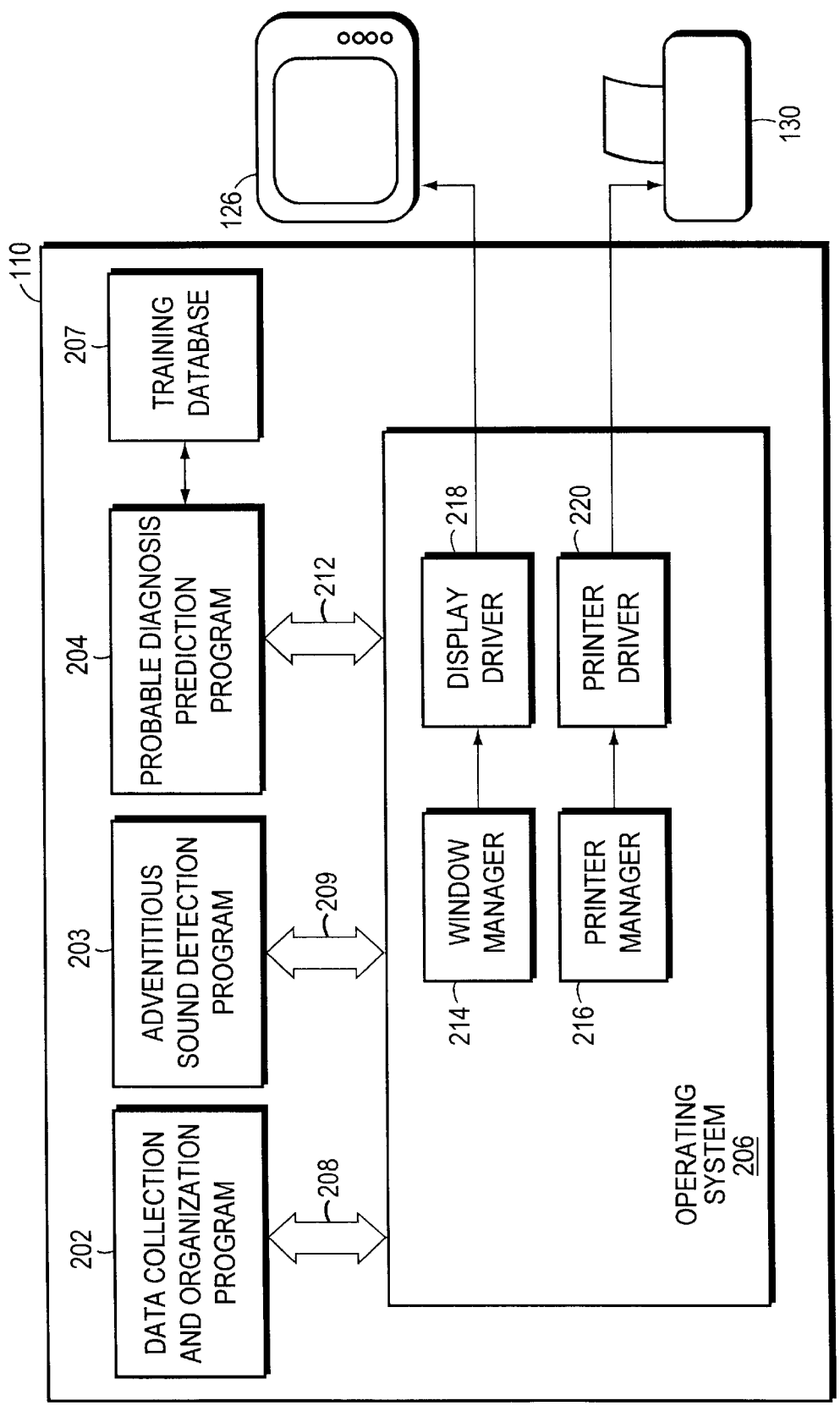
FIG. 2 is a block diagram of the computer station component of FIG. 1 illustrating the relationship of an operating system and several application programs.

FIG. 2 is a highly schematized illustration of the computer station 110 illustrating the interaction of several software elements, including a data collection and organization application program 202, an adventitious-sound detection program 203, a probable-diagnosis prediction program 204, and an operating system 206. The application programs 202–204 execute on the computer station 110. Interacting with the probable-diagnosis prediction program 204, moreover, is a training database 207. The application programs 202–204 and the operating system 206 interact, as shown by arrows 208, 209 and 212, via system calls to control the operations of the computer station 110.

Included within the operating system 206 are system facilities, including a window manager 214 and a printer manager 216, which, inter alia, implement at least some of the system calls. Lower layers of the operating system 206 (or the computer station 110) may also include device drivers, such as a display driver 218 and printer driver 220. Drivers 218, 220 interface directly with hardware components, such as the graphical user interface 126 and the printer 130, respectively.

It should be understood that computer station 110 may include additional application programs. It should be further understood that the computer station 110 may omit the adventitious-sound detection and/or the probable-diagnosis prediction programs 203, 204.

Data Collection and Organization

Figure 3:
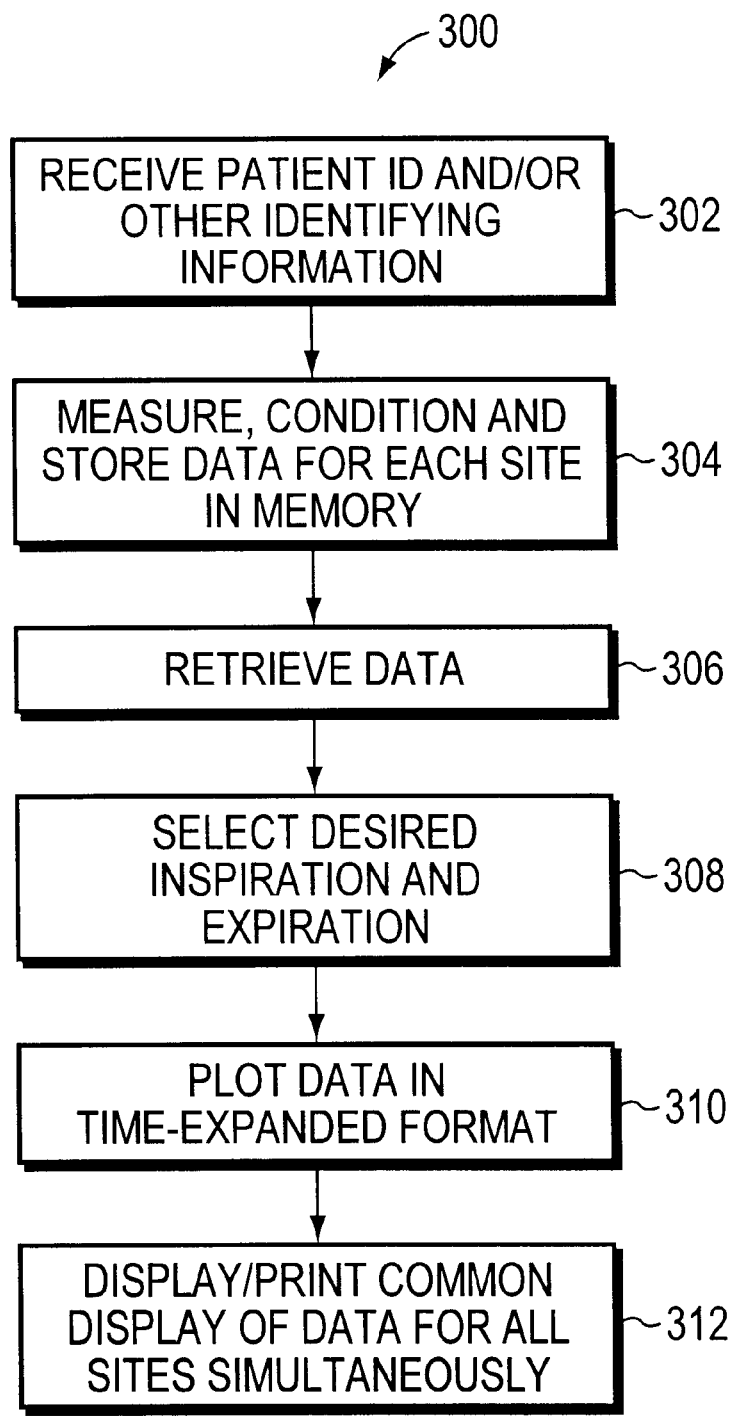
FIG. 3 is a flow chart of the steps performed by a data collection and organization application program.

In operation, the microphones 102 are preferably taped or strapped to the patient's skin at the sixteen sites. Next, the system 100 is initialized and the data collection and organization application program 202 is preferably opened. FIG. 3 represents a flow chart of operations 300 performed by the data collection and organization application program 202 (FIG. 2). As shown by block 302, the data collection and organization program 202 first requests patient identifying information (such as name, identification number, physician, etc.), which may be entered by a system operator through the keyboard 124 or mouse 122. This information may be displayed on the graphical user interface 126 in a data collection window (not shown). Next, the patient is instructed to breath in (inspiration) and out (expiration) several times. While the patient breathes, lung sounds detected by the microphones 102 are converted to audio signals and provided to the signal conditioning circuit 108. Preferably, data is continuously received for a sufficient period of time (e.g., ten seconds) to ensure that useful data is obtained for at least one inspiration/expiration pair. As indicated at block 304, the audio signals are measured, conditioned and provided to the analog-to-digital converter 132 for digitization. The digital data for each site is then stored at either the memory 114 of computer station 110 or the digital storage device 120. If fewer microphones are used, they may be situated at the next location(s) and the process repeated.

Next, the data collection and organization application program 202 retrieves the data for display or printing, as shown by block 306. Specifically, the data collection and organization application 202 interacts with the operating system 206 so as to retrieve the data corresponding to each site from memory 114 or the storage device 120. The data for each site, which represents both inspiration and expiration combined, is preferably displayed on screen 228. A preferred form of display is described below.

Figure 4:
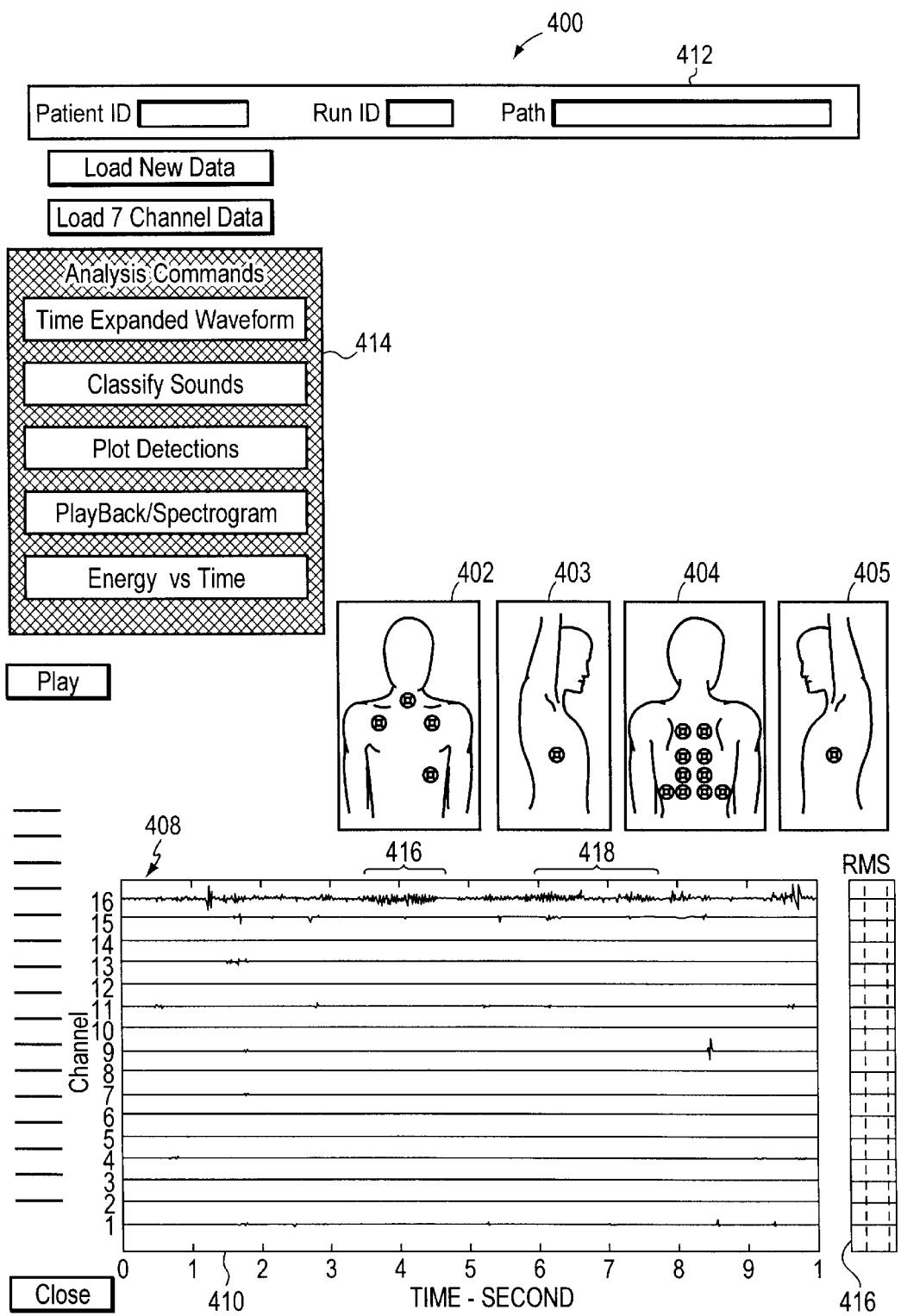
FIG. 4 is a representative display of data for a single location.

Next, as indicated by block 308 (FIG. 3), the system operator selects a particular inspiration and expiration for further analysis by identifying the corresponding starting and stopping points of the selected inspiration and expiration. Preferably, this is accomplished with the aid of a display formed in accordance with the present invention and illustrated in FIG. 4. FIG. 4 is a highly schematic representation of a preferred display 400 of data obtained from sixteen sites. The display 400 preferably includes a set of body maps 402–405, which illustrate the various sites at which data was recorded, and a data plot area 408, which contains an illustration of the recorded data. More specifically, the data plot area 408 includes the actual data tracings (i.e., signal tracings) obtained at each microphone 102 (FIG. 1) and preferably includes a corresponding time axis 410. The data in data area 408 corresponds to both inspiration and expiration combined and is preferably a plot of signal amplitude (e.g., millivolts or decibels) from the microphones 102, each associated with a particular channel number, versus time in seconds as shown by time axis 410. It should be understood that the display 400 may include other areas, such as a patient data area 412, a command bar area 414 and a root-mean-square (RMS) field 416.

To mark the starting and stopping points of the selected inspiration and expiration, the system operator moves a pointer (not shown) associated with the mouse 122 across the data area 408 to the start of inspiration and executes a mouse "click" at that location, thereby associating a particular time (based on the corresponding point on the time axis 410) with the start of inspiration. The data collection and organization application program 202 preferably includes conventional means to associate the position of the pointer with the time value vertically aligned therewith upon execution of the mouse click. The system operator similarly associates respective times with the end of inspiration and with the starting and stopping times of expiration. The starting and stopping points for inspiration and expiration are best identified by examining the signal or tracing recorded at the trachea microphone (i.e., microphone channel 16). In particular, inspiration is typically associated with a first continuous, high amplitude segment 416 of the trachea signal. When the amplitude of the segment 416 diminishes to near zero, inspiration is typically at an end. Expiration is similarly associated with a continuous, high amplitude segment 418 that directly follows inspiration segment 416. When the amplitude of this second continuous segment 418 diminishes to zero, expiration is typically complete.

It should be understood that the data collection and organization program 202 may as an alternative, or a supplement, to operator selection, include one or more modules or routines that automatically identify the starting and stopping points of inspiration and expiration in a similar fashion.

Following the identification of the starting and stopping points of a selected inspiration and expiration, the data collection and organization program 202 proceeds to organize the corresponding data for display as a function of time. In particular, as indicated by block 310 (FIG. 3), the program 202 preferably plots the data corresponding to each site for both inspiration and expiration in a time-expanded format. Execution of the time expansion function is preferably in accordance with the description set forth in U.S. Pat. No. 3,990,435, which is hereby incorporated by reference in its entirety. Specifically, the data collection and organization program 202 preferably generates two increments of time-expanded data: (i) slightly time-expanded and (ii) fully time-expanded. In particular, the data collection and organization program 202 modifies a copy of the data for each site obtained at step 304 so that it may be displayed or printed in a slightly time-expanded scale (e.g., on the order of 200–400 mm/sec.) and in a fully time-expanded scale (e.g., on the order of 800 mm/sec.) in addition to the more conventional, non-expanded time scale of around 20–50 mm/sec. As block 312 indicates, the data collection and organization program 202 then displays and/or prints-out the data corresponding to inspiration and expiration for each site (which is now maintained in three formats: (i) unexpanded, (ii) slightly time-expanded and (iii) fully time-expanded), in a common display, where it can be viewed in all formats simultaneously.

Figure 5A:
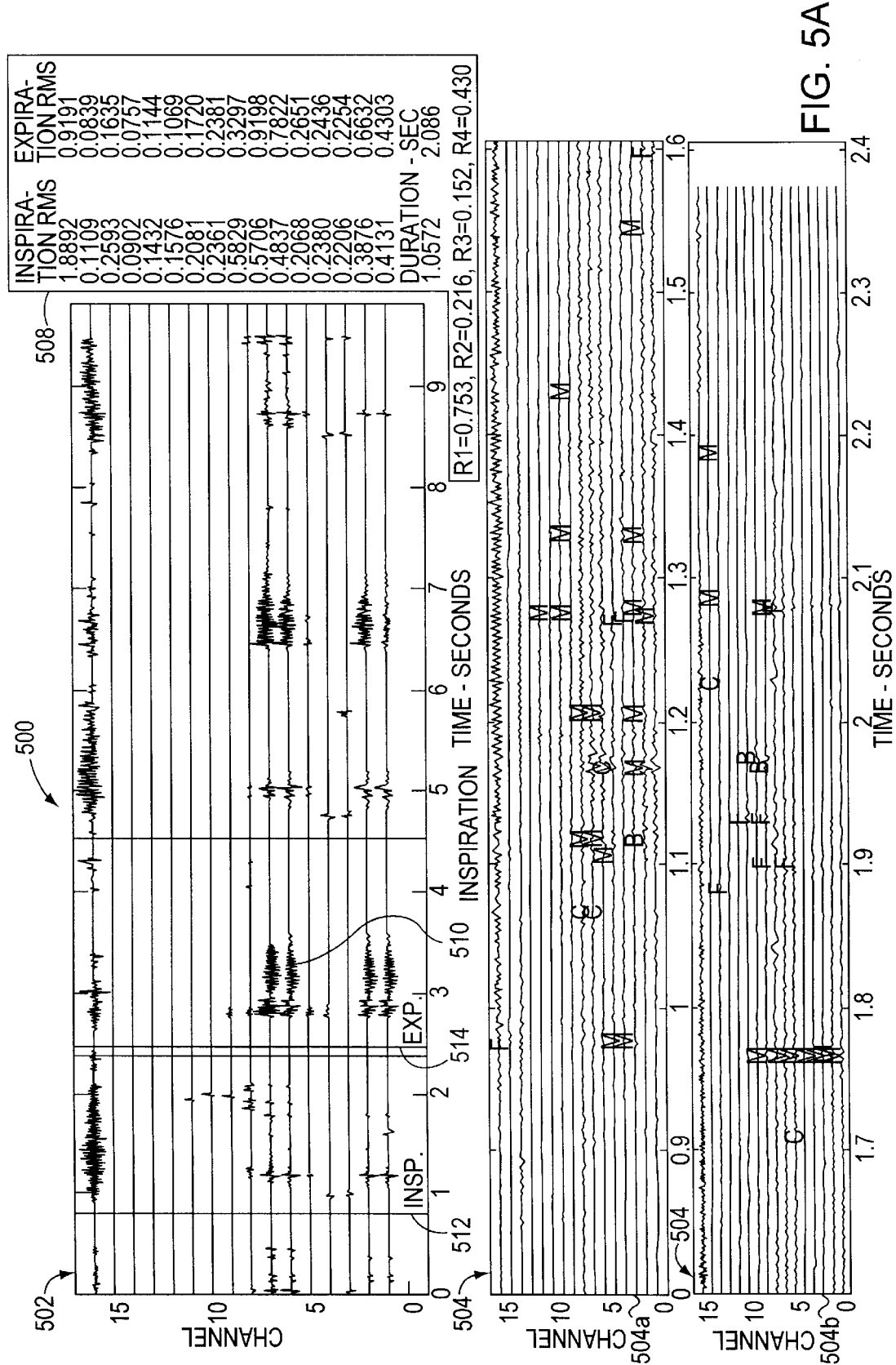
FIGS. 5A and 5B are a highly schematic representation of a combinational display of information in accordance with the present invention.
Figure 5B:
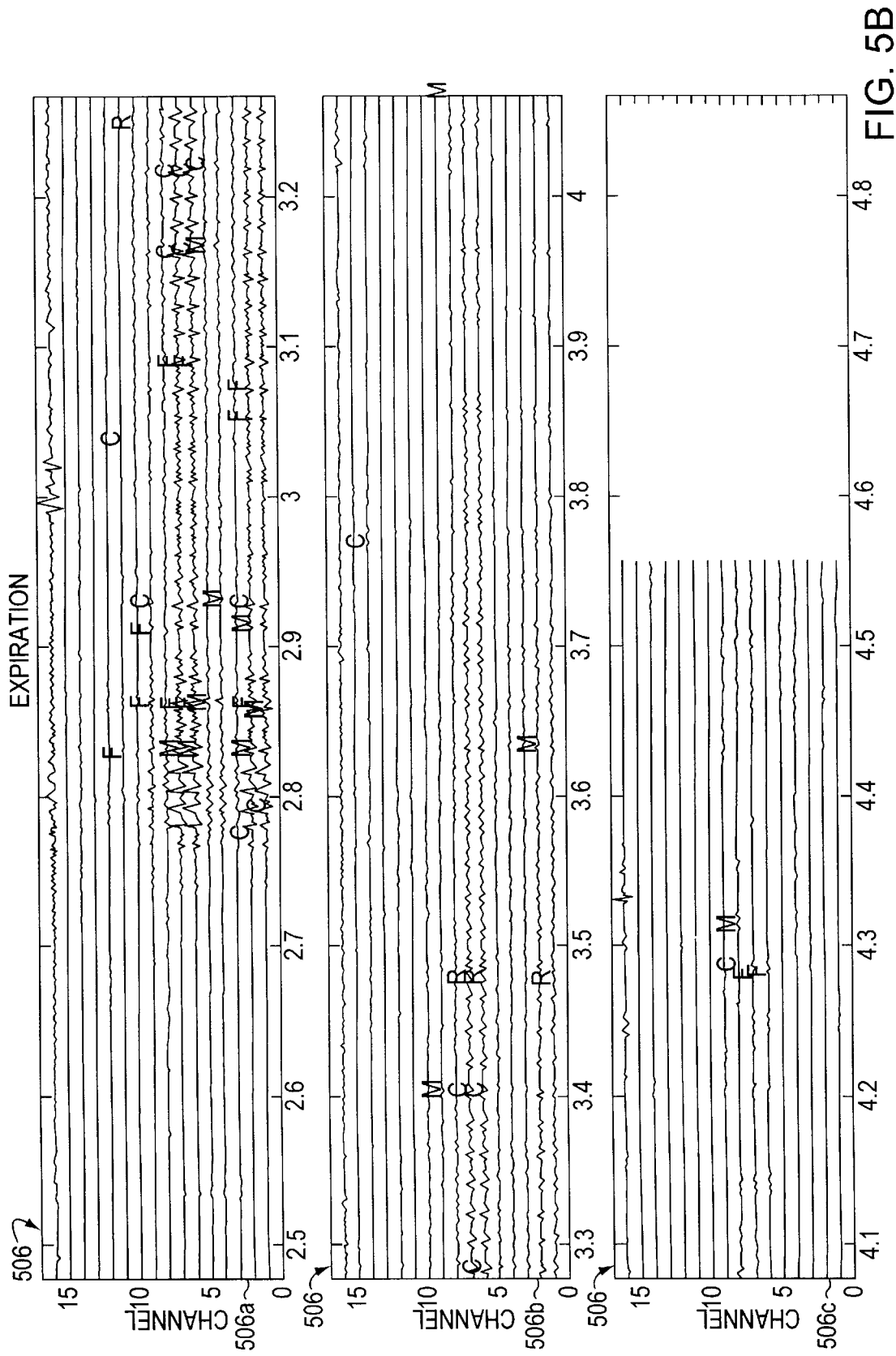

FIGS. 5A and 5B illustrate a highly schematic representation of a preferred combinational display or print-out 500 of lung sound data generated by the data collection and organization program 202. The combinational display 500 includes first, second and third plot elements 502, 504 and 506, respectively, and a data field 508. Each plot element 502, 504 and 506 includes a data or signal trace (e.g., trace 510 in first plot element 502) of the amplitude of the detected lung sounds (vertical axis) for each microphone as a function of time (horizontal axis). As mentioned above, the microphones 102 (FIG. 1) may be identified by channel (e.g., channels one through sixteen) at least one of which (e.g., channel sixteen) corresponds to the patient's trachea. Channels one to fifteen preferably represent the fifteen microphones each located at a different site around the patient's chest, as described above. The first plot element 502 represents the lung sound data for all inspirations and expirations over the predefined time period (e.g., ten seconds) combined in an unexpanded time scale. That is, the data is formatted for display at approximately 20–50 mm/sec. The time period represented by the first plot element 502 is preferably selected so that at least one set of inspiration and expiration data of sufficient quality is obtained. The previously selected inspiration and expiration are preferably enclosed within blocks located in the first plot element 502. In particular, the selected inspiration is enclosed in a first block 512 and the selected expiration is enclosed in a second block 514.

Second plot element 504 represents the lung sounds corresponding to the selected inspiration as detected by each microphone in a slightly time-expanded format. That is, the data is displayed on an approximately 200–400 mm/sec. scale. Depending on the length of the selected inspiration, second plot element 504 may comprise more than one (e.g., two) panels 504a and 504b. Similarly, the third plot element 506 represents the lung sounds corresponding to the selected expiration for each microphone also in a slightly time-expanded format. Since the selected expiration was adjacent to the selected inspiration, the time scale (horizontal axis) for the third plot element 506 continues on from the time scale for the second plot element 504. The third plot element 506 may also be represented by multiple panels, such as panels 506a, 506b and 506c, depending on its length. The signal tracings within the first, second and third plot elements 502, 504 and 506, moreover, are preferably arranged in a vertical stack configuration relative to each other.

The data field 508 preferably includes several computed quantities as determined from the selected inspiration and expiration information. More specifically, the data field 508 preferably contains a root-mean-square (RMS) value calculated in a conventional manner for each channel during the selected inspiration and expiration. The RMS values may be provided in column format adjacent to the first plot element 502. In addition, data field 508 may include the length of time of the selected inspiration 512 and the selected expiration 514, preferably in seconds. Data field 508 may further include other computed statistical quantities identified as R1, R2, R3 and R4, that are of interest to the attending physician. For example, R1 may represent the ratio of time of selected inspiration to time of selected expiration. R2 may be the ratio of R1 to the average RMS value at the trachea during inspiration. R3 may be the ratio of the average RMS value during inspiration for the microphones located on the chest to the RMS value for the trachea during inspiration. R4 may be the standard deviation of the RMS values during inspiration for all of the channels.

Once the recorded data has been displayed and/or printed in the manner illustrated in FIGS. 5A and 5B, it is preferably reviewed by the attending physician. As shown, the combinational display 500 concisely and effectively presents the data obtained at multiple sites to the attending physician. In particular, examination of plot elements 504 and 506, which represent the slightly time-expanded data, quickly reveals the occurrence of any adventitious sounds. Further review of these elements 504 and 506 provides detail information regarding the existence, identity and location of the adventitious sounds. For example, by simply referring to the corresponding channel number, a physician may quickly ascertain at which location an adventitious sounds was recorded. By arranging the signal tracings in a vertical stack as shown in the combinational display 500, he or she may also judge whether the same event produced adventitious sounds detected at more than one location. This may all be performed, moreover, without having to switch back-and-forth between a plurality of screens or sheets. That is, the data collection and organization application program 202 (FIG. 2), in cooperation with the operating system 206, may adjust the size of the plot elements 502, 504 and 506 so that they fit in their entirety in one or two windows on the display screen 228 or on one or two sheets of paper, if printed. Moreover, the system 100 may mark the location of detected adventitious sounds within the second and third plot elements 504 and 506, utilizing a set of abbreviations as identifiers, as described below. For example, "C" stands for a coarse crackle, "M" stands for a medium crackle, "F" for a fine crackle, "W" for a wheeze and "R" for rhonchi.

By comparing the data contained within combinational display 500 with information indicative of various pulmonary conditions or diseases, moreover, the physician may be able to render a diagnosis with a relatively high degree of accuracy. In particular, Table 1 lists the criteria or characteristics of lung sounds associated with four possible conditions: normal, COPD, asthma and IPF, based on empirical studies and analysis of numerous subjects with the indicated conditions. As shown in Table 1, for example, a normal patient's expiration should last about 20% longer than his inspiration. This information, moreover, may be quickly obtained by simply reviewing the R1 value in the data field 508. For a patient suffering COPD, expiration is typically on the order of 60% longer than inspiration.

TABLE 1

CHARACTERISTICS OF PULMONARY SOUND TRACINGS

| | Normal | COPD | Asthma | IPF |
|---|---|---|---|---|
| Ratio of Time of Inspiration to Time of Expiration | Expiration 20% longer than Inspiration (on average) | Expiration 60% longer than Inspiration (on average) | Expiration typically much longer than Inspiration | variable |
| Distribution of Sounds over the Patient's Chest | Relatively high amplitude of sounds during Inspiration, little or no variation in sound amplitude across the chest | Amplitude of sounds during Inspiration variable, but higher than amplitude of sounds during Expiration | Relatively uniform distribution of sounds across the chest, wheezes typically present | variable |
| Sounds Occurring During Inspiration | appear random | broken, irregular | wheezes typically present | crackles typically present |
| Occurrence of Abnormal Sounds During Inspiration and Expiration | few | wheezes and rhonchi typically present, early inspiratory crackles also common | prominent wheezing, rhonchi may also be present | many crackles typically present |

A diagram of illustrative adventitious or abnormal sounds may also be utilized by the attending physician, in combination with the information contained in Table 1, when reviewing combinational pulmonary display 500 so as to assist in arriving at a diagnosis. FIG. 6A is an exemplary plot of lung sound amplitude (vertical axis) versus time (horizontal axis) for a plurality of microphones illustrating the appearance of crackles. FIG. 6B is a similar exemplary plot illustrating the appearance of a wheeze. FIG. 6C is another exemplary plot illustrating the appearance of Type I and Type II rhonchus.

The preferred combinational display thus portrays the detected sounds so that the presence or absence of the characteristics specified in Table I may be ascertained. In particular, the combinational display portrays the following information: (1) the ratio of inspiration to expiration, preferably as a percentage; (2) the distribution of adventitious sounds over the chest and their relative amplitudes; (3) the occurrence of adventitious during inspiration and expiration; and (4) whether the adventitious sounds are crackles, wheezes or rhonchi. As shown, the preferred display 500 provides all of this information to the attending physician in a coherent, efficient manner.

Figure 7:
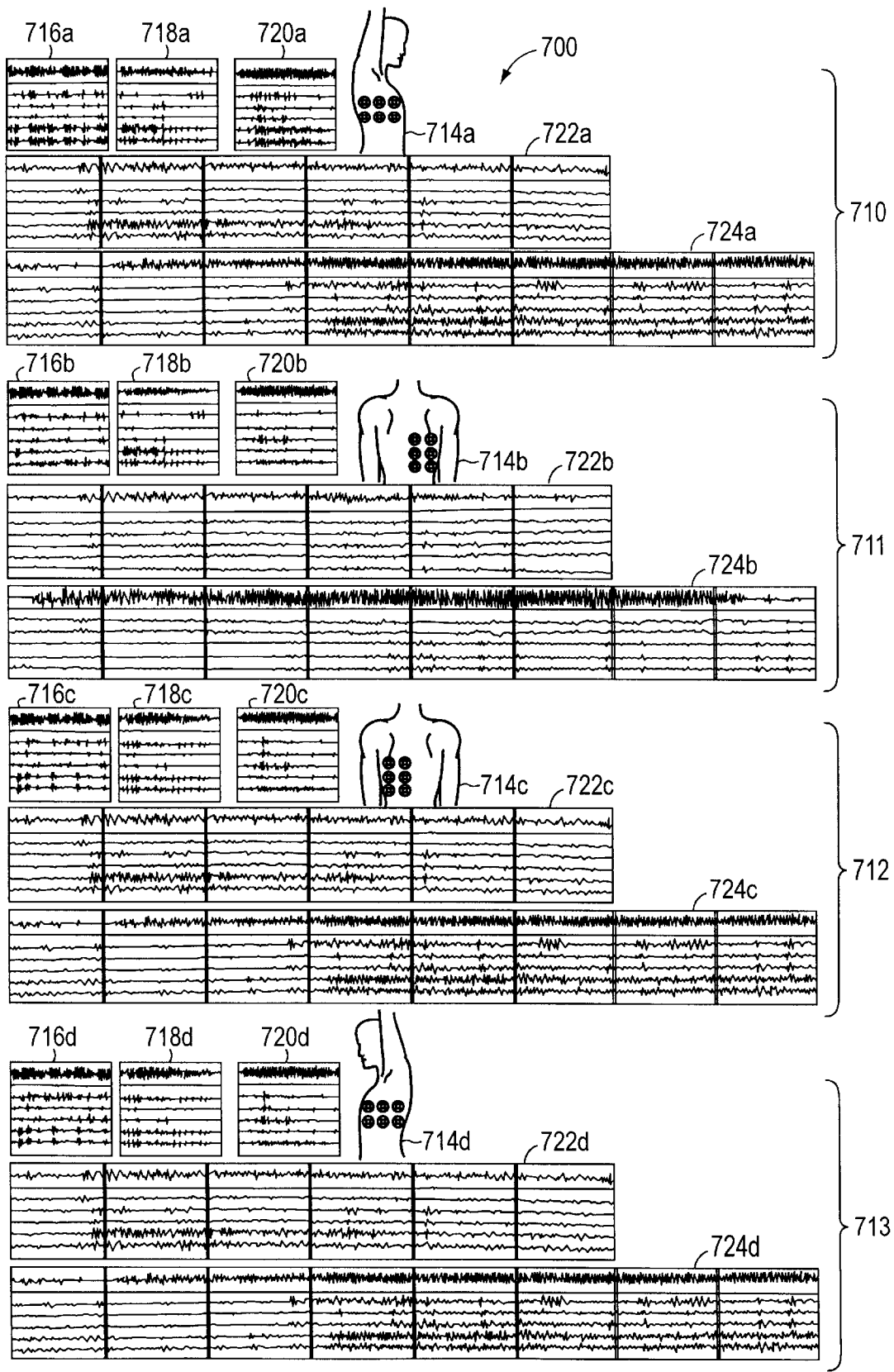
FIG. 7 is a highly schematic representation of another combinational display of information.

Nonetheless, it should be understood that other combinational displays may be generated by the system. For example, FIG. 7 is a highly schematic representation of another combinational display or print-out 700 of data by the data collection and organization program 202 (FIG. 2) from block 312. As shown, data from four chest regions (right back, left back, right side and left side) is simultaneously portrayed either on the graphical user interface 128 and/or printed preferably on a single sheet of paper from printer 130. The combinational display 700 is preferably divided into four sections 710–713, each corresponding to a particular chest region at which data was obtained. Within each section 710–713, moreover, may be a graphical body illustration 714a–714d, corresponding to the particular chest region at which the respective data was obtained. For example, graphical illustration 714b, associated with the data in section 711, corresponds to the patient's right back region.

Each section 710–713 preferably includes a representation of the data in multiple time scales and formats. In particular, a first display element 716a–716d, disposed with each section 710–713, respectively, illustrates the data obtained at each microphone for several repetitions of inspiration and expiration combined in an unexpanded time scale. That is, the data is formatted for display at approximately 20–50 mm/sec. A second display element 718a–718d, similarly disposed within each section 710–713, respectively, illustrates the data obtained at each microphone for inspiration only in a slightly expanded scale (e.g., on the order of approximately 200–400 mm/sec.). A third display element 720a–720d illustrates the data obtained by each microphone during expiration only, also in a slightly expanded scale (e.g., on the order of approximately 200–400 mm/sec.).

A fourth display element 722a–722d illustrates inspiration only for each microphone in a fully expanded time scale. That is, the data is displayed on an approximately 800 mm/sec. scale. A fifth display element 724a–724d, corresponding to each section 710–713, respectively, illustrates the data for expiration only, also in a fully expanded scale. In the preferred embodiment, the first through third display elements (i.e., elements 716, 718 and 720) are all preferably arranged side-by-side above display element 722. Additionally, display element 724 corresponding to fully expanded expiration, which is often the longest, is preferably arranged below display element 722 and may wrap around as necessary.

Other arrangements of the display elements 716–724 forming combinational display 700 may also be employed. Nonetheless, all of the display elements 716–724 are preferably arranged so as to be shown simultaneously. That is, all of the display elements 716–724 are preferably arranged to appear on the graphical user interface 128 at the same time and/or printed on a single sheet of paper.

To ensure that the display elements 716–724 of combination pulmonary display 700 are placed on the graphical user interface 128 at the same time and/or preferably printed on a single sheet of paper, the data collection and organization application 202 (FIG. 2), in cooperation with the operating system 206, may adjust the size of the display elements 716–724 so that they will fit in their entirety either on the graphical user interface 128 or on a sheet of paper. Nonetheless, the relative relationships between unexpanded, slightly time-expanded, and fully time-expanded are preferably maintained.

The arrangement of information within the combinational display 500 or 700 facilitates various disease diagnosis by highlighting their distinctive and identifying characteristics to the attending physician. In addition, the above-described procedure, unlike x-rays or exploratory surgery, presents little risk or discomfort to the patient.

Adventitious-Sound Detection

In a preferred embodiment, the computer station 110 (FIG. 2) further includes an adventitious-sound detection program 203, as mentioned above. The adventitious-sound detection program 203 preferably parses the data recorded by each microphone 102 (FIG. 1) to identify the occurrence of any adventitious sounds, such as crackles, wheeze or rhonchi. The adventitious-sound detection program 203 preferably operates in accordance with the methods and procedures described in U.S. Pat. No. 5,165,417 entitled LUNG SOUND DETECTION SYSTEM AND METHOD to Raymond L. H. Murphy, Jr., the inventor herein, which is also incorporated by reference herein in its entirety.

More specifically, the consecutive waves of each sound signal are preferably analyzed to determine when a particular wave meets established predefined amplitude and cycle period criteria. Once such a wave is identified, the next adjacent waves are similarly analyzed to determine whether they meet other predefined cycle period and/or amplitude criteria. Depending on the number of consecutive waves that are found to meet particular period and/or amplitude requirements, the adventitious sound detection program 203 may categorize these portions of the signal as crackles, wheeze, rhonchi, or other adventitious sound, depending on the criteria that were utilized in setting the thresholds.

Figure 8:
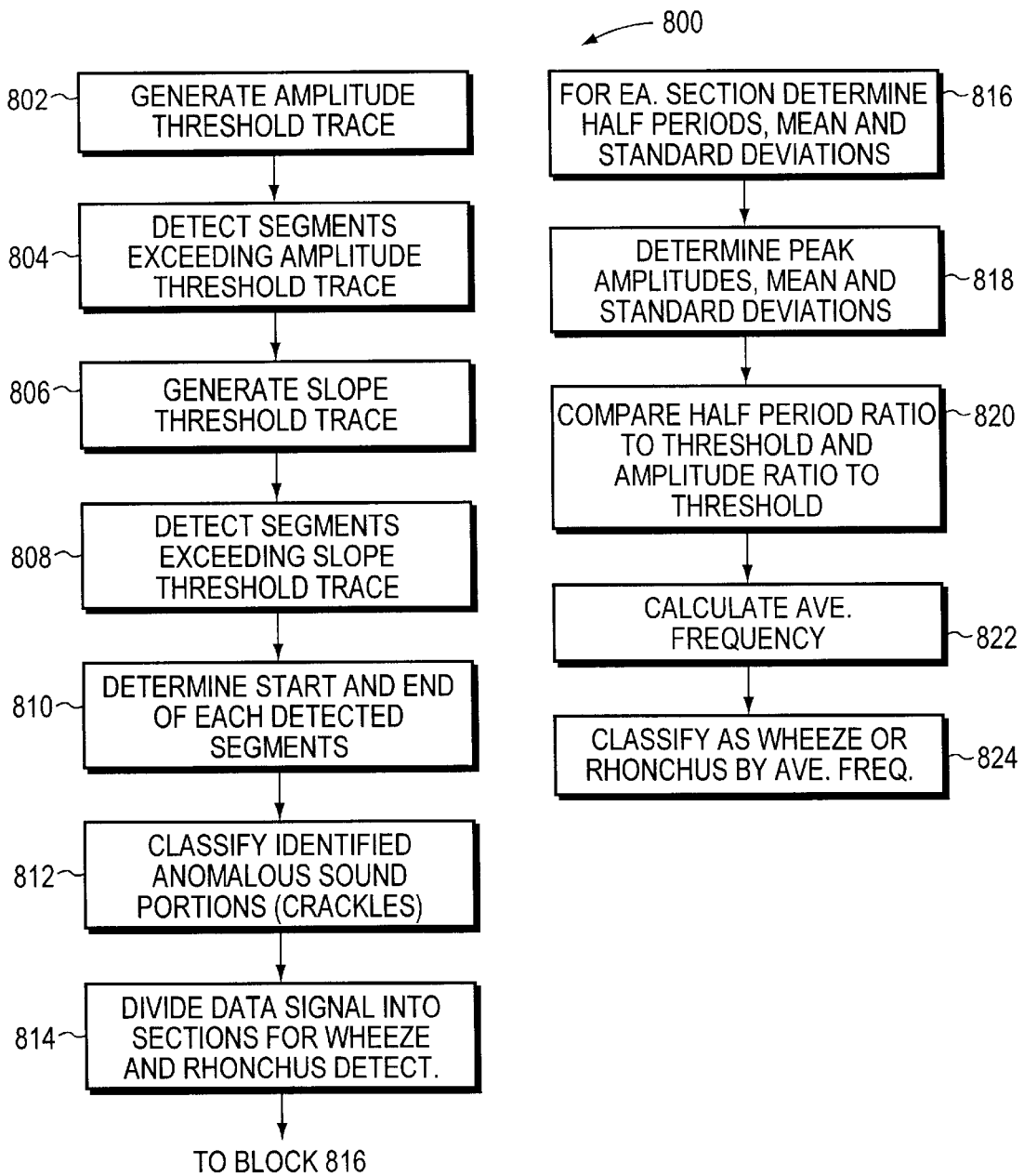
FIG. 8 is a flow chart of the steps performed by an adventitious-sound detection application program.

For example, FIG. 8 is a flow chart of operations 800 executed by the adventitious-sound detection program 203. At block 802, the program 203 first generates a corresponding amplitude threshold trace for the data signal (i.e., signal trace) corresponding to each site. To generate the amplitude threshold trace, the program 203 first determines a running average amplitude trace corresponding to the absolute value of the signal over 600 data points (e.g., 300 data points on either side of the data point for which the running average is currently being calculated). As described above, information from the microphones 102 is preferably sampled at 8000 data points per second. The program 203 proceeds to determine the mean of the running average amplitude trace which is then multiplied by an amplitude threshold constant (e.g., 1.5). The amplitude threshold constant is used to distinguish adventitious sounds, such as crackles, from background lung noise. Empirical studies have shown that an amplitude threshold constant of 1.5 is adequate to distinguish crackle events in most cases, although other values may also be employed. The resulting value is added to the running average amplitude trace to form an amplitude threshold trace. FIG. 9A is a data plot 902 for a particular microphone 102 (FIG. 1) which represents either inspiration or expiration plotted as a function of time. The data plot 902 includes a data signal 910 and a corresponding amplitude threshold trace 912, generated as described above. As shown, the data signal 910 exceeds the amplitude threshold trace 912 at various points (e.g., points A, B, C, etc.). The adventitious-sound detection program 203, at block 804 (FIG. 8), next compares the data signal 910 (FIG. 9A) to the corresponding amplitude threshold trace 912 and, for each portion of the data that exceeds the corresponding threshold, stores a corresponding index or identifier of that portion of the data.

Next, program 203 similarly identifies portions of the data signal that exceed a signal slope threshold. Specifically, the program, at block 806 (FIG. 8), generates a corresponding slope threshold trace. More specifically, the program 203 calculates the first difference of the data trace using a difference equation. A preliminary slope threshold trace is then formed by calculating the running average over 600 data points. The median of the preliminary threshold trace is then determined and the median is multiplied by a slope threshold constant (e.g., 0.15). The slope threshold constant is chosen to distinguish adventitious sounds from discrete sound artifacts (such as machine noise, skin noises, etc.) that may be present in the signal trace and may also have rapidly rising slopes. Again, empirical studies have shown that a slope threshold constant of 0.15 is adequate in most cases to distinguish adventitious sound events from sound artifacts.

The resulting value is then added to the preliminary threshold trace to form a slope threshold trace.

FIG. 9B is a data plot 920 for a particular microphone 102 (FIG. 1) plotted as a function of time. The data plot 920 includes a slope data signal 922 and a corresponding slope threshold trace 924, generated as described above. As shown, the slope data signal 922 exceeds the slope threshold trace 924 at various points (e.g., points D, E, F, etc.).

Returning to FIG. 8, the adventitious-sound detection program 203, at block 808, next compares the slope data signal 822 (FIG. 9B) to the corresponding slope threshold trace 924 and, for each portion of the signal that exceeds the corresponding threshold, stores a corresponding index or identifier of that portion of the signal.

Program 203 next proceeds to determine the start and end of each "anomalous" signal segment detected in steps 804 and 808 above. In particular, as shown at block 810, for each segment of the data trace that exceeded the amplitude threshold trace, program 203 may define the end as the first zero crossing after the last point at which the amplitude threshold was exceeded. To determine the start, program 203 preferably locates the earliest slope exceeding point that occurs before the first amplitude exceeding point and defines the start as the zero crossing before the located slope exceeding point. If no corresponding slope exceeding point is found, the portion is not considered to be a crackle event.

After identifying the start and end of each anomalous signal segment within a given signal, program 203, at block 812, is ready to further analyze and classify the various signal segments. In particular, program 203 may first determine the number of zero crossings that are present in the subject anomalous signal segment. If the number of zero crossings is greater than 4 but less than 8, program 203 next proceeds to calculate the first three half periods of the signal portion and computes an average detection width as the mean of the three half period values. If the third half period is longer than the second half period, then program 203 preferably classifies the sound portion as a crackle. Other criteria may optionally or additionally be used to classify sound segments as crackles. For example, a crackle may be defined as having an initial deflection width or a maximum deflection width that exceeds a predefined threshold or a number of sequential deflection widths that exceed some threshold. Additionally, if the computed average detection width (or the initial or maximum deflection widths) is between 0.0015 and 0.0025 seconds, the sound portion is classified as a fine crackle. If the computed average detection width is between 0.0025 and 0.0035 seconds, the sound portion is classified as a medium crackle and if the average detection width is between 0.0035 and 0.0045 seconds, the sound portion is classified as a coarse crackle.

To identify wheezes and rhonchi, program 203 preferably proceeds as follows. First, as shown at block 814, program 203 divides the inspiratory or expiratory data signal corresponding to each site into sections, which may each be ⅛ second in duration. Next, at block 816, program 203 determines all half periods of the zero crossings of the signal, and the mean and standard deviations of the half periods for each section. Similarly, at block 818, program 203 determines the peak amplitudes of each half cycle and the mean and the standard deviation of the peak amplitudes for each segment. These measured half periods and peak amplitudes are then compared to predefined criteria. As indicated by block 820, if the ratio of the standard deviation of half period to mean half period is less than a predefined threshold (e.g., 0.4) and, if the standard deviation of peak amplitude over mean peak amplitude is less than another predefined threshold (e.g., 0.4), the subject segment is classified as a wheeze or rhonchus. To differentiate between wheezes and rhonchi, program 302, at block 822 calculates the average frequency of the segment (i.e., 1/{2* mean half period}) and, at block 824, compares the average frequency to a predefined threshold (e.g., 120 Hz). In particular, if the average frequency is less than 120 Hz, program 203 classifies the segment as a rhonchus. If the average frequency is greater than 120 Hz, program 203 classifies the segment as a wheeze.

It should be understood that other detection algorithms or techniques may be implemented by the system 100.

Following the detection of adventitious sounds as described above, the system 100 may display the results to the system operator and/or the attending physician. For example, the system 100, through adventitious sound detection program 203, may label sections of the signals contained in the second and third plot elements 504 and 506 (FIGS. 5A and 5B) at which adventitious sounds were detected. In particular, the system 100 may mark the location of detected adventitious sounds, utilizing a set of abbreviations as identifiers. For example, "C", stands for a coarse crackle, "M" stands for a medium crackle, "F" for a fine crackle, "W" for a wheeze and "R" for rhonchi.

Figure 10:
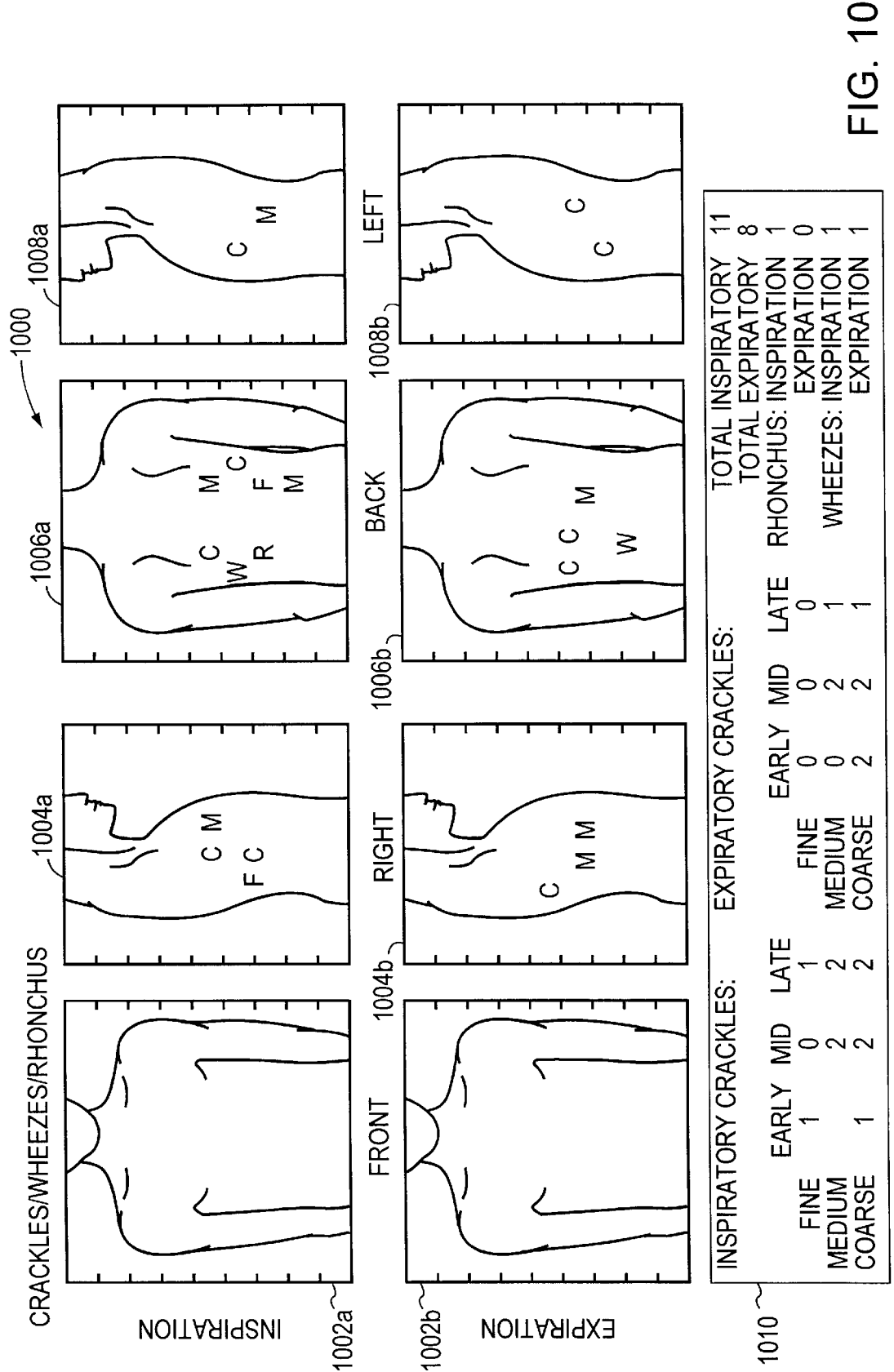
FIG. 10 is a highly schematic illustration of a graphical display showing the points at which abnormal sounds were detected.

The system 100 may also generate additional body plots either on graphical user interface 128 or in print form to illustrate the location of the detected adventitious sounds. FIG. 10 is a highly schematic illustration showing the location of detected crackles, wheezes, and/or rhonchi. Specifically, a graphical depiction 1000 preferably includes a set of body plots 1002a–1008a for inspiration and a similar set of body plots 1002b–1008b for expiration. In particular, the body plots preferably correspond to a patient's front 1002, right side 1004, back 1006 and left side 1008 chest regions. Again, utilizing a set of abbreviations as identifiers, the system 100 marks the location of detected adventitious sounds.

In addition to the body plots, the graphical depiction 1000 may also include a summary field 1010. Located within the summary field 1010 may be information relating to the total number of fine, medium, and coarse crackles that were detected for inspiration and expiration. The number of crackles may be further defined as having occurred early (e.g., first third), mid (e.g., middle third) or late (e.g., last third) of either inspiration and expiration as a function of time. Similarly, the total number of wheezes and rhonchi that were detected during inspiration and expiration may also be provided within the summary field 1010 of graphical depiction 1000.

Figure 11:
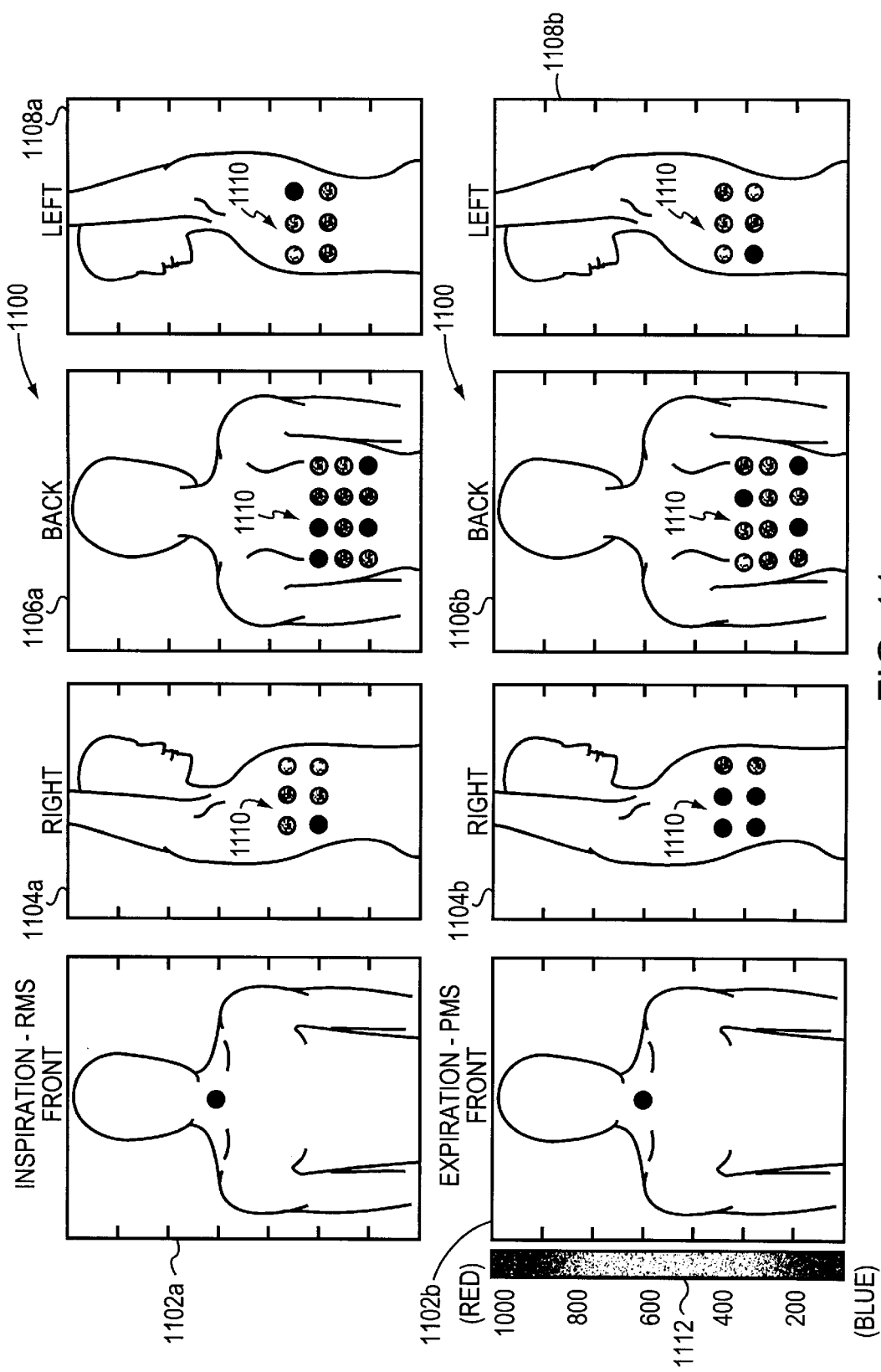
FIG. 11 is a highly schematic illustration of a graphical display showing sound intensity levels as determined by the present invention.

As mentioned above, application program 203 may further determine a root-mean-square (RMS) level for the inspiratory and expiratory portion of the signal from each microphone. The RMS levels provide the attending physician with a mechanism for comparing the intensity of the lung sounds as recorded at each microphone. The computed RMS values, moreover, may be displayed on graphical user interface 128 (FIG. 1) in tabular or graphical form. Referring to FIG. 11, program 203 preferably generates an RMS graphical display 1100 having a first set of body plots 1102a–1108a each corresponding to a particular chest region (e.g., front, right, back and left) for inspiration and a second set of body plots 1102b–1108b similarly corresponding to a particular chest region for expiration. Within each body plot 1102–1108 is a set of markers 1110 each corresponding to a particular microphone site. Each marker 1110, moreover, is preferably color-coded to reflect the intensity of the computed RMS level for that site. A color coded scale 1112 of RMS levels is also provided, where blue corresponds to relatively low RMS intensity levels and red corresponds to relatively high RMS intensity levels.

Review of graphical display 1100 by the attending physician may provide substantial information. For example, the presence of fluid in a patient's pleural space (i.e., the area between the chest wall and the lungs and against which the lungs slide) has been found to cause a marked decrease in sound intensity over the affected area. The identification of this condition may be rapidly and accurately determined by means of a review of display 1100. In particular, areas with relatively low RMS values (i.e., low sound intensity) are indicated in display 1100 by blue designations 1110. Accordingly, the presence of fluid in the pleural space often manifests as blue designations 1110, especially where adjacent red designations (i.e., areas of high sound intensity) are also present.

It should be understood that, for a given signal trace, separate RMS values may be calculated for those portions of the signal trace representing adventitious sounds and those portions which do not correspond to adventitious sounds.

Probable-diagnosis Prediction Program

In the preferred embodiment, the system 100 (FIG. 1) further includes a probable-diagnosis prediction program 204 (FIG. 2), which reviews the results obtained from the adventitious-sound detection program 203 and preferably provides a proposed diagnosis based upon those results. This program 204 may be based on a neural network module, such as the neural network programming tools from The Mathworks, Inc. or other statistical classification methods. The probable-diagnosis prediction program 204 preferably interacts with a training database 207 to derive the proposed diagnosis. In particular, the training database 207 preferably contains a set of adventitious lung sound data from patients previously diagnosed with various pulmonary diseases, such as COPD, asthma, IPF, etc. More specifically, the training database 207 includes typical data corresponding to the ratio of inspiration to expiration, the numbers and locations of coarse, medium, and fine crackles, wheezes, and rhonchi, and RMS values commonly associated with these diseases. The probable-diagnosis prediction program 204 compares the results obtained by the adventitious-sound detection program 203 for the given patient with the information in the training database and provides a proposed diagnosis, which represents the particular disease which most closely matches the results obtained for the given patient.

It should be understood that the probable-diagnosis prediction program 204 may alternatively utilize multiple logistic regression models to arrive at a proposed diagnosis. A suitable multiple logistic model approach is described in P. Bettencourt, E. Del Bono, D. Spiegelman, E. Hertzmark and R. Murphy, Jr. *Clinical Utility of Chest Auscultation in Common Pulmonary Diseases* Vol. 150, No. 5 American Journal of Respiratory and Critical Care Medicine (November 1994), which is hereby incorporated by reference in its entirety.

The foregoing description has been directed to specific embodiments of this invention. It will be apparent, however, that other variations and modifications may be made to the described embodiments with the attainment of some or all of their advantages. Accordingly, this description should be taken only by way of example and not by way of limitation. It is the object of the appended claims to cover all such variations and modifications as come within the true spirit and scope of the invention.

What is claimed is:

1. A lung sound diagnostic system for use in analyzing lung sounds detected during at least one of the inspiration and expiration of a patient by a detection system for detecting lung sounds at at least six sites around the patient's chest, the system comprising:

means for receiving data corresponding to the lung sounds detected at each site; and means, responsive to the received data, for generating a combinational pulmonary display including a first display element having a time domain plot of the lung sounds detected at each site during at least one of inspiration and expiration as a function of a first time scale, wherein the plot of lung sounds within the first element are simultaneously arranged in a vertical stack configuration.

2. The lung diagnostic system of claim 1 wherein the detection system includes at least six sound transducers each placed at a different one of the sites.

3. The lung diagnostic system of claim 1 wherein the detection system includes at least eight sound transducers each placed at a different one of the sites.

4. The lung sound diagnostic system of claim 1 wherein the combinational pulmonary display further includes a second display element having a time domain plot of the lung sounds detected at each site for at least one of inspiration and expiration as a function of a second time scale, such that the second time scale is slightly expanded relative to the first time scale.

5. The lung sound diagnostic system of claim 4 further comprising means for calculating the duration of inspiration and expiration and the combinational pulmonary display further includes a data field having a first value corresponding to the calculated duration of inspiration and a second value corresponding the calculated duration of expiration.

6. A lung sound diagnostic system comprising:

one or more transducers for generating signals responsive to lung sounds at a plurality of sites around a patient's chest;

means, coupled to the transducers, for determining an intensity of the sound at each site; and means for generating a common display which displays the sound intensity at each of the sites, wherein the sound intensity determining means is configured to calculate a root-mean-square (RMS) value of the signal generated from each site, the display generating means generates one or more body plots, each body plot having a marker associated with each site, and the markers reflect the intensity of the calculated RMS value as calculated for that site.

7. The lung sound diagnostic system of claim 6 wherein each of the markers is color coded.

8. The lung diagnostic system of claim 6 wherein body plot includes at least one. schematic representation of a patient's chest area.

9. The lung sound diagnostic system of claim 6 wherein the body plot includes at least one front view of a patient's chest area.

10. The lung sound diagnostic system of claim 6 wherein the body plot includes at least one side view of a patient's chest area.

11. The lung sound diagnostic system of claim 6 having at least six transducers, each placed at a different site; around the patient's chest.

12. The lung sound diagnostic system of claim 6 having at least eight transducers, each placed at a different site around the patient's chest.

13. A lung sound diagnostic system comprising:
- a plurality of transducers that may be placed at various sites around a patient's chest for generating signals responsive to lung sounds;
- means, coupled to the plurality of transducers, for determining whether the signals generated by the transducers meet predefined criteria associated with one or more adventitious lung sounds; and
- means for generating a common display having at least one body plot with markers thereon that identify one or more patient chest locations at which the respective signals met the pre-defined criteria.

14. The lung diagnostic system of claim 13 further comprising means for identifying one or more types of adventitious lung sounds wherein the markers are coded to specify which type of adventitious lung sound was identified.

15. The lung diagnostic system of claim 13 having at least six transducers, each placed at a different site around the patient's chest.

16. The lung diagnostic system of claim 13 having at least eight transducers, each placed at a different site around the patient's chest.

17. The lung sound diagnostic system of claim 13 wherein the determining means comprises means for calculating the average frequency of at least a segment of the signals and means for classifying the segment as a wheeze or a rhonchi by comparing the average frequency of the segment against a predefined threshold.

18. The lung sound diagnostic system of claim 17 wherein, the classifying means classifies the segment as a rhonchi if the average frequency is less than approximately 120 Hz and a wheeze if the average frequency is greater than approximately 120 Hz.

19. A method for collecting, organizing and displaying lung sound information during at least one of the inspiration and expiration of a patent comprising:
- placing a plurality of transducers at various sites around a patient's chest for generating signals responsive to lung sounds;
- receiving signals from the plurality of transducers;
- determining whether the received signals meet predefined criteria associated with one or more adventitious lung sounds; and
- generating a common display having at least one body plot with markers thereon that identify one or more patient chest location at which the respective signal met the predefined criteria.

\* \* \* \* \*